(12) United States Patent
Dowaki (10) Patent No.: US 8,687,190 B2
(45) Date of Patent: Apr. 1, 2014

(54) FINE PARTICLE DETECTOR AND LIGHT EMITTING APPARATUS

(75) Inventor: Suguru Dowaki, Kanagawa (JP)

(73) Assignee: Sony Corporation, Tokyo (JP)

( * ) Notice: Subject to any disclaimer, the term of this patent is extended or adjusted under 35 U.S.C. 154(b) by 285 days.

(21) Appl. No.: 13/180,736

(22) Filed: Jul. 12, 2011

(65) Prior Publication Data

US 2012/0019824 A1  Jan. 26, 2012

(30) Foreign Application Priority Data

Jul. 20, 2010  (JP) ................................. 2010-162853

(51) Int. Cl.
 *G01N 21/00* (2006.01)
(52) U.S. Cl.
 USPC .......................................... 356/337; 356/338
(58) Field of Classification Search
 None
 See application file for complete search history.

(56) References Cited

FOREIGN PATENT DOCUMENTS

| JP | 2007-46947 | | 2/2007 |
|---|---|---|---|
| JP | 2010060687 | A * | 3/2010 |

\* cited by examiner

*Primary Examiner* — Gregory J Toatley
*Assistant Examiner* — Amanda Merlino
(74) *Attorney, Agent, or Firm* — K&L Gates LLP (57) ABSTRACT

A fine particle detector includes a light emitting system letting light from a light source pass through a phase difference element and focusing the light on a sample flow through which fine particles flow. When the direction of the sample flow is an X-axis direction, the light is emitted to the sample flow in a Z-direction, and a ZX-plane is orthogonal to a Y-direction, then the phase difference element has a plurality of regions divided in the Y-axis direction and causes a phase difference between wavefronts of the light passing through the plurality of regions.

6 Claims, 8 Drawing Sheets

Prior Art

FIG. 8

Prior Art

US 8,687,190 B2

FINE PARTICLE DETECTOR AND LIGHT EMITTING APPARATUS

CROSS REFERENCES TO RELATED APPLICATIONS

The present application claims priority to Japanese Priority Patent Application JP 2010-162853 filed in the Japan Patent Office on Jul. 20, 2010, the entire contents of which are hereby incorporated by reference.

BACKGROUND

The present application relates to a fine particle detector and a light emitting apparatus, and more particularly, to a fine particle detector or the like that optically analyzes the characteristics of fine particles such as cells or microbeads.

A fine particle detector of the related art emits light (laser) to fine particles flowing in a flow cell or in a flow channel formed on a microchip, detects scattered light from the fine particles or fluorescence generated from the fine particles themselves or fluorescent material marked on the fine particles, and measures the optical characteristics of the fine particles. In addition, this fine particle detector separately collects the population determined to meet predetermined conditions from the fine particles, as a result of the measurement of optical characteristics. Of such fine particle detectors, the apparatus that measures the optical characteristics of cells as fine particles or separately collects the cell population that meets predetermined conditions is particularly called a flow cytometer, cell sorter, etc.

For example, Japanese Unexamined Patent Application Publication No. 2007-46947 discloses the flow cytometer that including a plurality of light sources that emits a plurality of excitation light beams each having a different wavelength and a different phase at predetermined time intervals and including a waveguide member that guides the plurality of excitation light beams to the same entrance optical path and focuses the plurality of light beams on dyed particles. This flow cytometer includes a plurality of light sources that emit a plurality of excitation light beams each having a different wavelength, a waveguide member that guides the plurality of excitation light beams to the same entrance optical path and focuses the plurality of excitation light beams on dyed particles, and a plurality of fluorescence detectors that detect fluorescence generated from the dyed particles excited by the plurality of excitation light beams and output fluorescence signals (see claims 1 and 3 and FIGS. 1 and 3 in the Japanese Unexamined Patent Application Publication No. 2007-46947).

Figure 6:
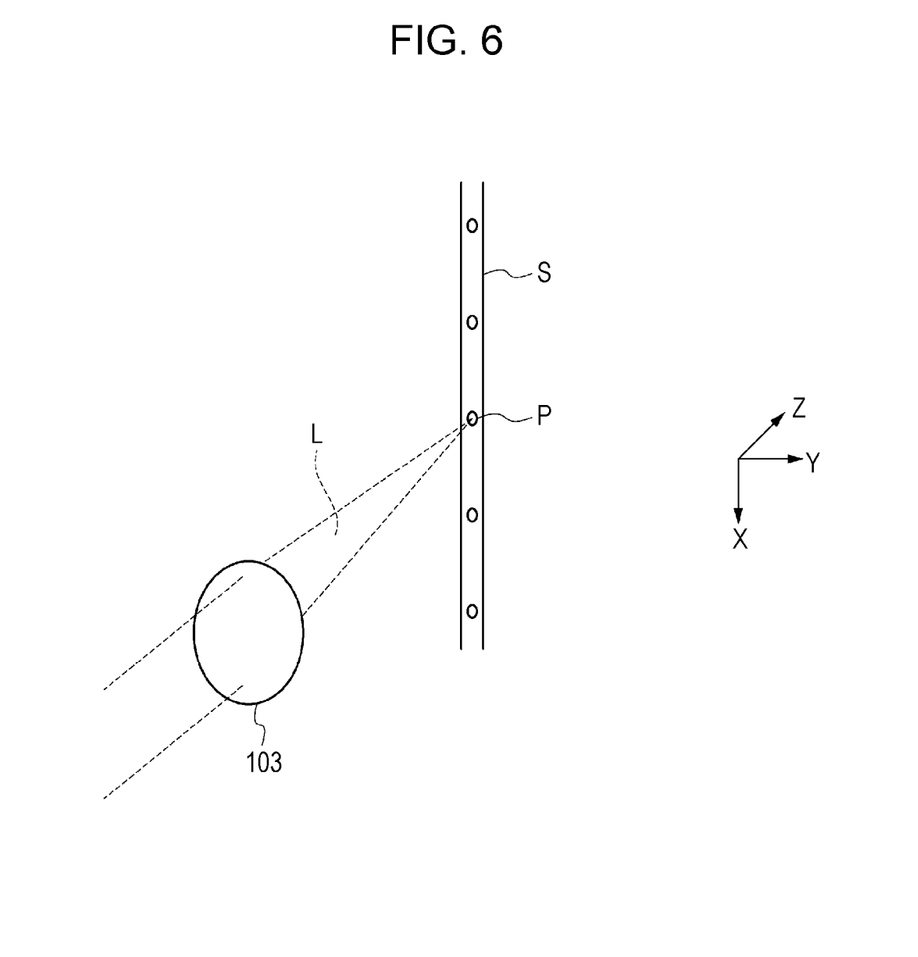
FIG. 6 is a schematic diagram showing the structure of a light emitting system of a fine particle detector of the related art.
Figure 7:
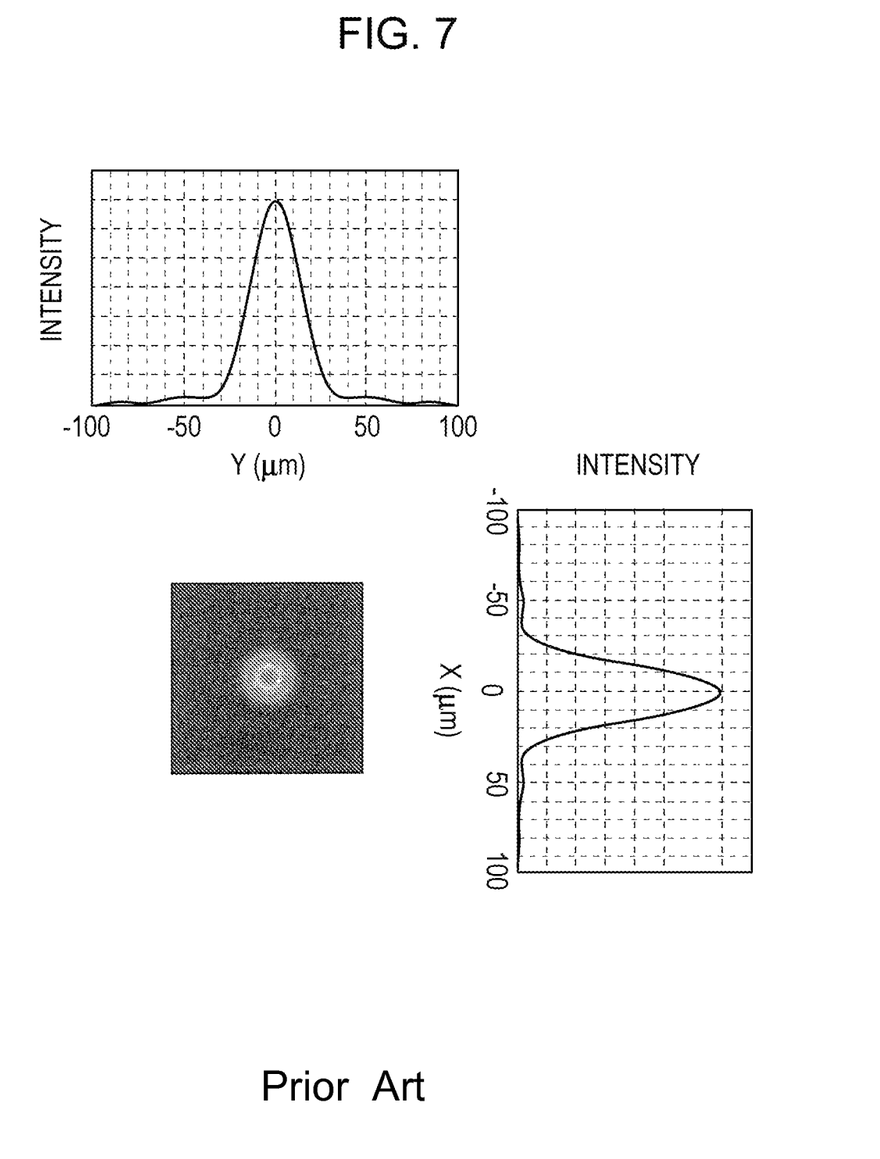
FIG. 7 shows the strength distribution in a laser spot of the fine particle detector of the related art.

In the fine particle detector of the related art, as shown in FIG. 6, a laser L is focused on a sample flow S by a focusing lens 103, and fine particles P flow through the sample flow S so as to cross the spot of the laser L focused. At this time, the strength distribution in the laser spot becomes a Gaussian distribution, in which the strength is large in the center of the laser spot and reduces significantly in the periphery. FIG. 7 shows an example of the strength distribution in a laser spot for the fine particle detector of the related art. If there are variations in the flow positions of a fine particle P in the sample flow S, the effective strength of the laser emitted differs between the fine particle P passing the center of the laser spot and the fine particle P passing the peripheral of the laser spot, thereby introducing error in the signal strength obtained.

SUMMARY

In the related art, in order to eliminate measurement error caused by variations in the flow position of a fine particle in the sample flow, the shape of the spot of a laser focused on the sample flow is deformed in the width direction (Y-axis direction in FIG. 6) of the sample flow to an ellipse. Since the strength distribution in the laser spot becomes a Gaussian distribution that is widened in the width direction of the sample flow in the strength distribution in this elliptic spot, differences in the laser strength between fine particles due to variations in the flow position in the sample flow can be suppressed.

Even when the spot shape is deformed to an ellipse, however, if the flow pressure of the sample flow is raised to increase the measurement speed, the flow width of the sample flow is further widened with respect to the elliptic spot, thereby making it difficult to stably equalize the effective strength of the laser emitted to the particles.

It is desirable to provide a technique for achieving high-precision and high-speed measurement by forming a laser spot with a uniform strength distribution over a wide range to equalize the effective strength of the laser to be emitted to fine particles in a sample flow.

According to an embodiment, there is provided a fine particle detector that includes a light emitting system letting light from a light source pass through a phase difference element and focusing the light on a sample flow through which fine particles flow, wherein, when the direction of the sample flow is an X-axis direction, the light is emitted to the sample flow in a Z-direction, and a ZX-plane is orthogonal to a Y-direction, then the phase difference element has a plurality of regions divided in the Y-axis direction and causes a phase difference between wavefronts of the light passing through the plurality of regions.

This fine particle detector lets the light emitted from the light source pass through the phase difference element and causes phase different between wavefronts of the light passing through the plurality of regions divided in the Y-axis direction in order to focus the laser spot of light focused by a focusing lens on the sample flow by widening the laser spot in the Y-axis direction.

In the fine particle detector, the phase difference element is divided into three regions in the Y-axis direction and causes a phase difference between a wavefront of light passing through a middle region and each of wavefronts of light passing through regions at both ends. In this case, the phase difference between the wavefront of light passing through the middle region and each of the wavefronts of light passing through the regions at both ends is π and the spot diameter of the light passing through the middle region is preferably 25% to 75% of the spot diameter of the light passing through the phase difference element.

According to an embodiment, there is provided a light emitting apparatus that lets light from a light source pass through a phase difference element having a plurality of regions divided and causing a phase difference between wavefronts of light passing through the plurality of regions and focuses the light on an object.

In an embodiment, fine particles widely include biometric fine particles such as cells, microorganisms, and liposomes or synthetic materials such as latex particles, gel particles, and industrial particles.

Biometric fine particles include chromosomes, liposomes, mitochondria, organelles (cell organelles), and other components of various types of cells. Target cells include animal cells (such as blood cells) and plant cells. Microorganisms include bacteria such as colon bacilli, viruses such as tobacco mosaic viruses, fungi such as yeast, etc. Biometric fine particles include biometric high polymers such as nucleic acid, protein, complexes thereof.

Industrial particles may be, for example, organic or inorganic polymeric material or metal. Organic high polymers include polystyrene, styrene, divinylbenzene, polymethylmethacrylate, etc. Inorganic high polymers include glass, silica, magnetic material, etc. Metal includes gold colloid, aluminum, etc. These fine particles are generally spherical, but may be non-spherical, and their size and weight are not also restricted particularly.

An embodiment provides a technique for achieving high-precision and high-speed measurement by forming a laser spot with a uniform strength distribution over a wide range to equalize the effective strength of the laser to be emitted to fine particles in a sample flow.

Additional features and advantages are described herein, and will be apparent from the following Detailed Description and the figures.

DETAILED DESCRIPTION

Embodiments of the present application will be described below in detail with reference to the drawings.
1. Fine particle detector according to an embodiment
2. Fine particle detector according to another embodiment
1. Fine particle detector according to an embodiment Each of FIGS. 1A and 1B shows the structure of a light emitting system of a fine particle detector according to an embodiment.

Figure 1A:
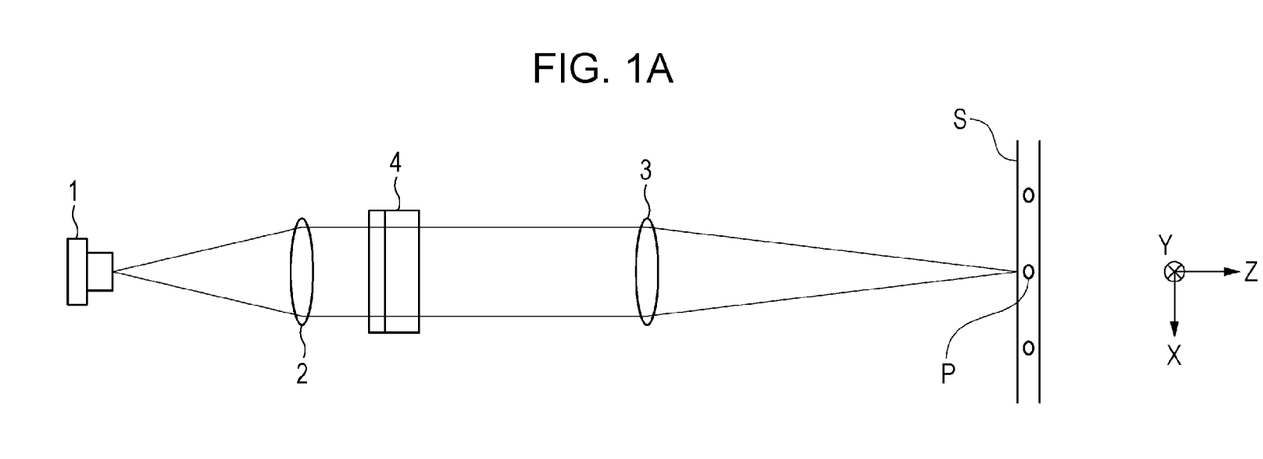
FIGS. 1A and 1B are schematic diagrams showing the structure of a light emitting system of a fine particle detector according to an embodiment.
Figure 1B:
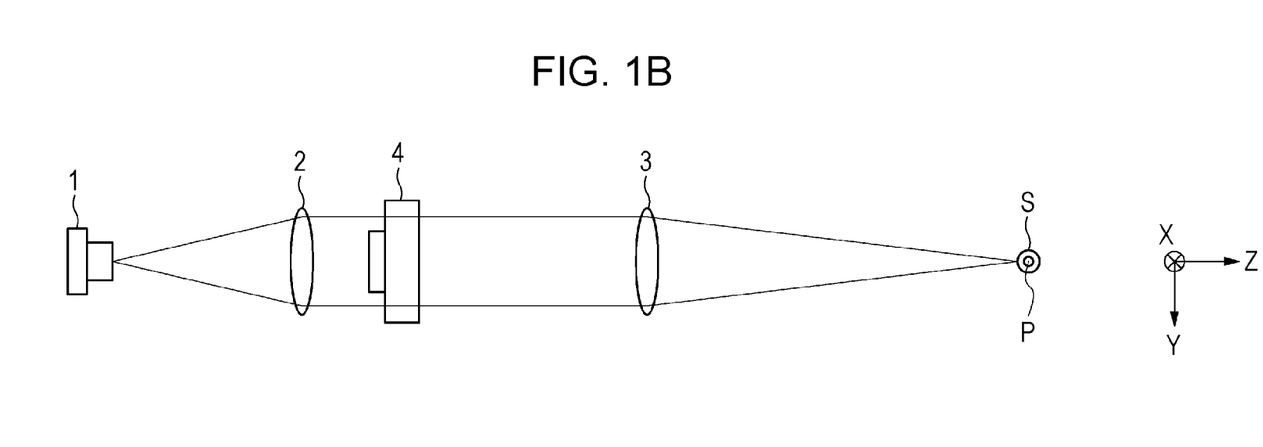

In FIGS. 1A and 1B, light (laser) emitted from a light source 1 is coupled into substantially parallel light by a collimator lens 2, passes through a phase difference element 4, and is focused by a focusing lens 3 on a sample flow S through which fine particles P flow. The sample flow S may be transferred in a flow cell or in a flow channel formed on a microchip. Here, it is defined that the direction of the sample flow S is the X-axis direction, the direction in which light is emitted to the sample flow S is the Z-axis direction, and the direction orthogonal to the ZX-plane is the Y-axis direction.

Scattered light or fluorescence generated from fine particles P or fluorescent material marked on the fine particles P by the light focused on and emitted to the sample flow S is detected by a light detection system (not shown). The light detection system may include an object lens, filter, mirror, light detector, etc. and its structure may be the same as that of the fine particle detector of the related art. Electrical signals from the light detector are used to measure the optical characteristics of the fine particles P. As a parameter for measurement of the optical characteristics, forward-scattered light is used when the size of the fine particle P is determined, backward-scattered light is used when the structure is determined, and fluorescence is used when presence or absence of fluorescence material marked on the fine particles P is determined, as in the fine particle detector of the related art.

Figure 2:
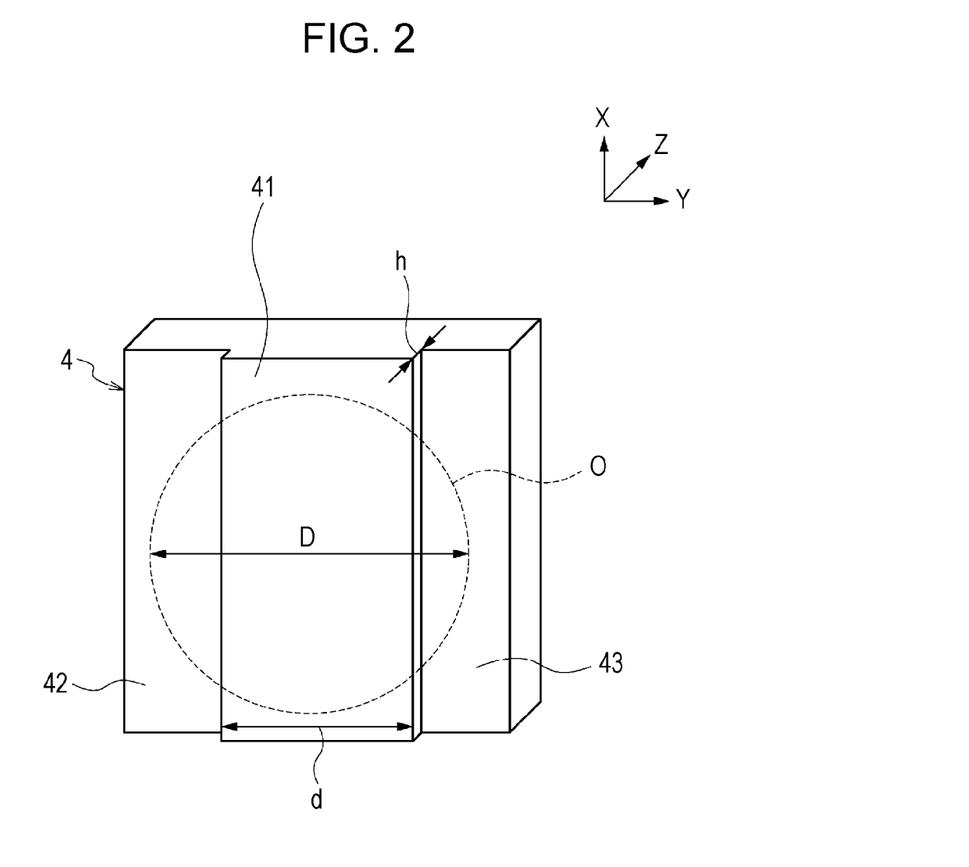
FIG. 2 is a schematic diagram showing the structure of a phase difference element.

FIG. 2 shows the structure of the phase difference element 4. In this drawing, reference symbol O shows the spot of light passing through the phase difference element 4 and reference symbol D shows its diameter.

The phase difference element 4 is divided into a plurality of regions in the Y-axis direction. These regions are a first region 41 in the middle and a second region 42 and a third region 43 at both ends. Reference symbol d indicates, of spot diameter D of light passing through the phase difference element 4, the part of the spot diameter D that passes through the first region 41.

The first region 41 has a physical step raised from the second and third regions 42 and 43 and, in this structure, phase difference π is caused between the wavefront of light passing through the first region 41 and each of the wavefronts of light passing through the second and third regions 42 and 43. That is, the height (indicated by h in FIG. 2) of the phase difference between the first region 41 and the second and third regions 42 and 43 meets the following expression. The height h of the phase difference between the first region 41 and the second and third regions 42 and 43 may project from the second and third regions 42 and 43 as shown in FIG. 2, or may dent from the second and third regions 42 and 43.

$$h \times (r-1) = \pi$$

(Symbol r in this expression indicates the refractive index of material included in the first region 41.)

When the phases of the wavefronts of light entering the focusing lens are aligned with each other, the light is focused on one point by the focusing lens. On the other hand, when the phases of the wavefronts of light entering the focusing lens are not aligned, the light is not focused on one point, but focused on a larger range. The fine particle detector according to the embodiment lets light emitted from the light source 1 pass through the phase difference element 4, causes phase differences between the wavefronts of light passing through the regions divided in the Y-axis direction, and widens the laser spot of light focused by the focusing lens 3 in the Y-axis direction.

Figure 3:
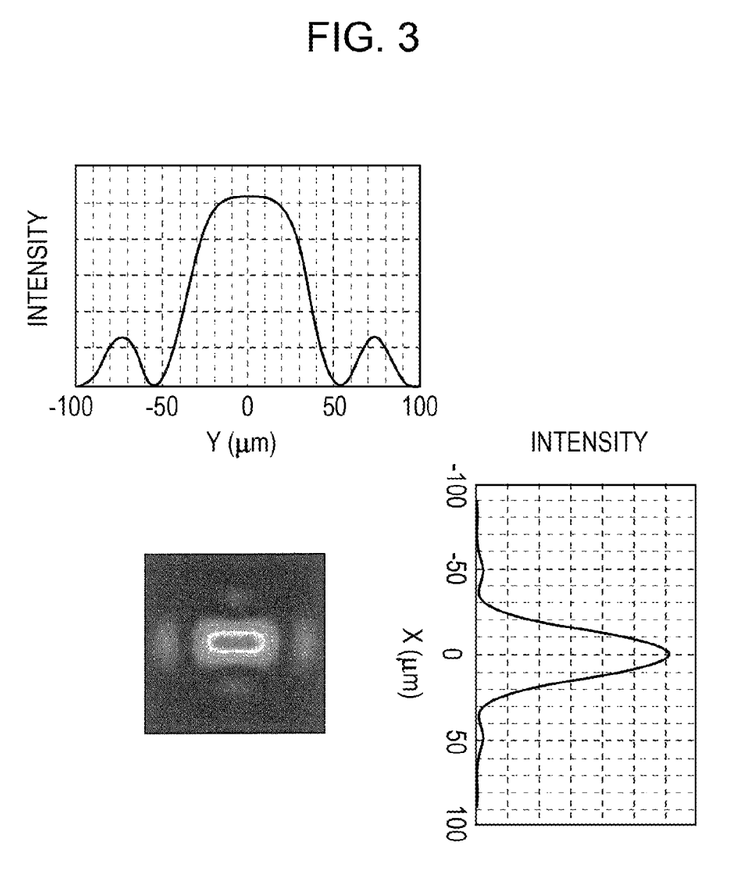
FIG. 3 shows the strength distribution in a laser spot of the fine particle detector according to the embodiment.

FIG. 3 shows an example of the strength distribution in a laser spot focused on the sample flow S in the fine particle detector according to the embodiment.

This drawing shows the result of calculation (simulation) for obtaining the strength distribution in the laser spot focused on the sample flow S when the light source 1 of a 638 nm band semiconductor laser has a divergence angle of 9 degrees in the X-axis direction and the Y-axis direction, the numerical aperture of the collimator lens 2 is 0.05, and the numerical aperture of the focusing lens 3 is 0.01. In this calculation, spot diameter d of light passing through the first region 41 is 70% of spot diameter D of light passing through the phase difference element 4.

In this drawing, the laser spot has a Gaussian distribution in the X-axis direction and has a strength distribution that is flat in the middle and uniform over a wide range in the Y-axis direction.

In the fine particle detector according to the embodiment, spot diameter d of light passing through the first region 41 is preferably 25% to 75% of spot diameter D of light passing through the phase difference element 4. Spot diameter d of light passing through the first region 41 is set to a value in this range, so that light passing through the individual regions can be focused as a laser spot that is flat in the middle and has a consecutively constant strength over a wide range in the Y-axis direction.

Figure 8:
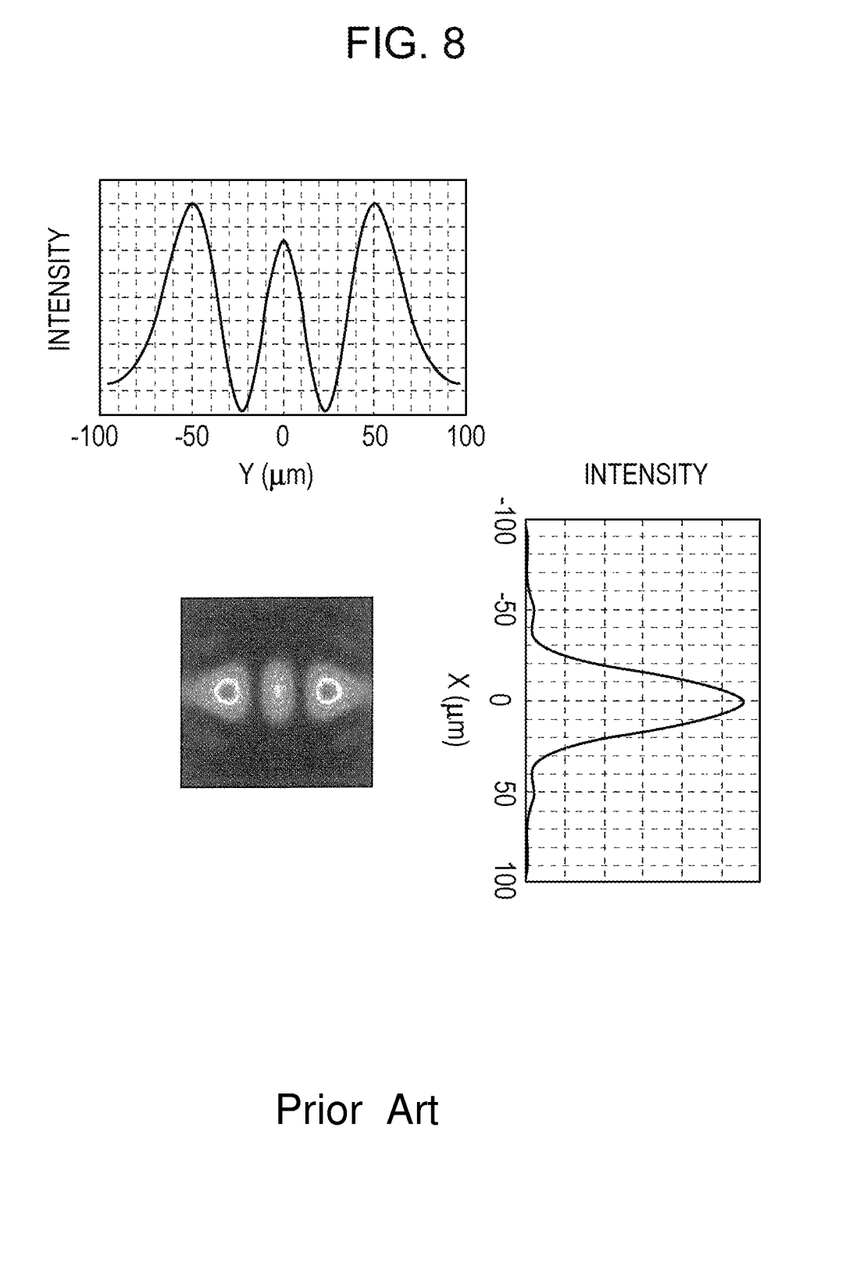
FIG. 8 shows the strength distribution in an inappropriate laser spot formed with the spot diameter of a laser passing through a first region in the fine particle detector according to the embodiment set to be 20% of the spot diameter of a laser passing through the phase difference element.

For comparison, FIG. 8 shows the strength distribution of a laser spot obtained as a result of calculation when spot diameter d of light passing through the first region 41 is assumed to be 20% of spot diameter D of light passing through the phase difference element 4. The laser spot is divided in the Y-axis direction and shows a nonuniform strength distribution.

As described above, in the fine particle detector according to the embodiment, a laser can be focused on the sample flow S as a spot that is widened in the Y-axis direction and has a uniform strength distribution over a wide range. Accordingly, the fine particle detector according to the embodiment can make the strength distribution in the laser spot a Gaussian distribution that is widened in the width direction (the Y-axis direction) of the sample flow S, and effectively suppress differences in laser emission strength between fine particles P that are caused by differences in the flow position in the sample flow S. High-precision and high-speed measurement can be achieved by elimination of measurement error caused by differences in the flow positions of fine particles P in the sample flow S.

Although the first region 41 is provided with a physical step to cause a phase difference between the wavefront of light passing through the first region 41 and the wavefronts of light passing through the second and third region 42 and 43 in the embodiment, a phase difference can also be caused by liquid crystal molecules with optical anisotropy. That is, liquid crystal molecules with optical anisotropy are arranged in the first region 41 and in the second and third regions 42 and 43 so that the alignment for the first region 41 differs from that for the second and third regions 42 and 43. Then, a phase difference may be provided by letting light pass through the phase difference element as linearly polarized light to cause a difference in the refractive index between the first region 41 and the second and third regions 42 and 43. It is also possible to control the alignment of liquid crystal molecules by sandwiching the liquid crystal molecules between ITO films and controlling the voltage of the first region 41 separately from the voltage of the second and third regions 42 and 43. In this case, the voltages are controlled to determine whether the embodiment is applied or not, so that the strength distribution of the laser spot can be switched between a normal Gaussian distribution and a Gaussian distribution widened in the width direction of the sample flow S.

Although the phase difference element 4 is divided into three regions in the Y-axis direction in the embodiment, the number of regions of the phase difference element 4 may be four or more as long as the effects of the embodiment are ensured. In addition, phase difference caused between the wavefronts of light passing through the regions are not limited to $\pi$ above and can be changed if necessary as long as the effects of the embodiment are ensured.

2. Fine particle detector according to another embodiment

Figure 4A:
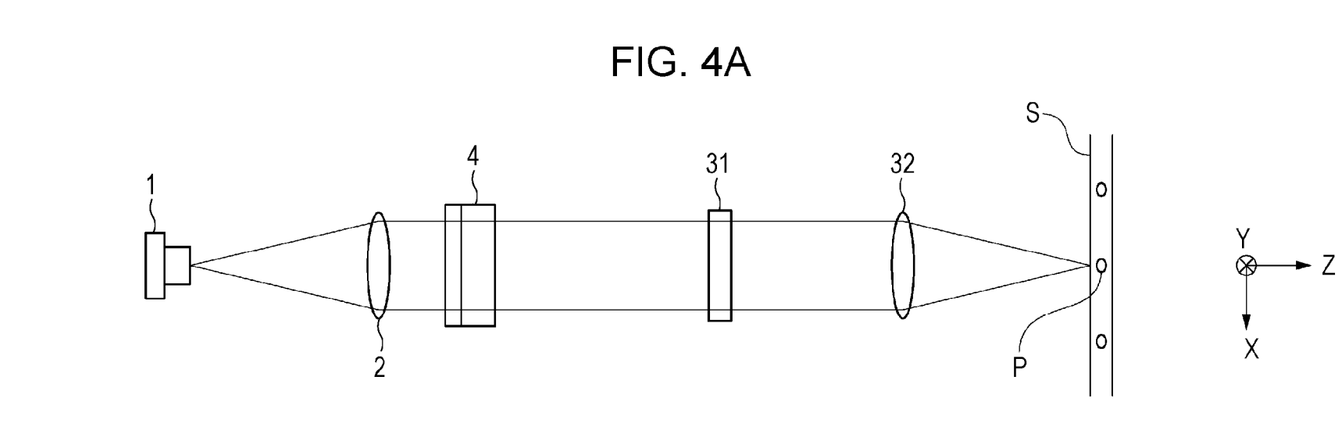
FIGS. 4A and 4B are schematic diagrams showing the structure of a light emitting system of a fine particle detector according to another embodiment.
Figure 4B:
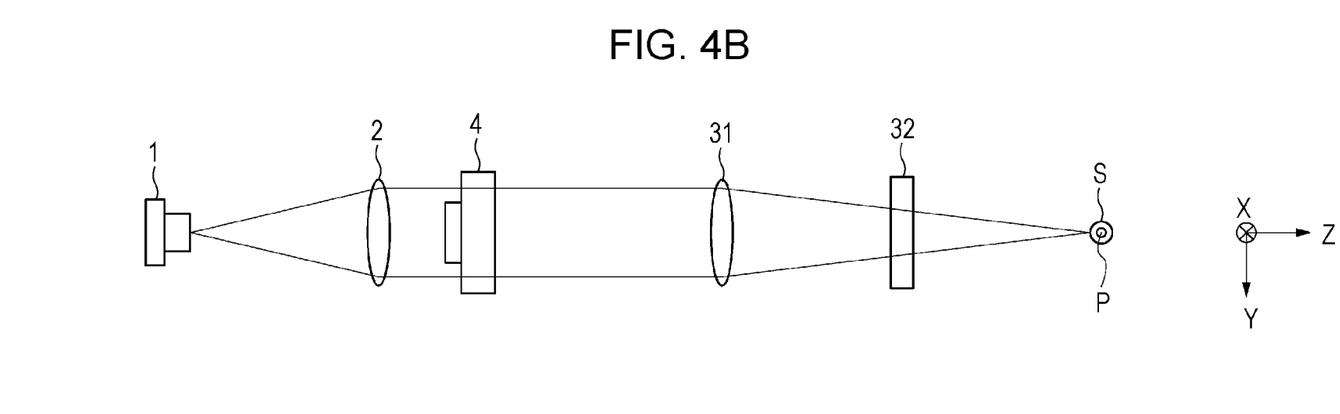

Each of FIGS. 4A and 4B shows the structure of a light emitting system of a fine particle detector according to another embodiment.

In FIGS. 4A and 4B, light (laser) emitted from the light source 1 is coupled into substantially parallel light by a collimator lens 2, passes through the phase difference element 4, and is focused on the sample flow S through which fine particles P flow by a pair of cylinder lenses 31 and 32 whose generatrices are orthogonal to each other. The sample flow S may be transferred in a flow cell or in a flow channel formed on a microchip. Here, it is defined that the flow direction of the sample flow S is the X-axis direction, the direction in which light is emitted to the sample flow S is the Z-axis direction, and the direction orthogonal to the ZX-plane is the Y-axis direction.

In the fine particle detector according to the other embodiment, the structure of the phase difference element 4 and the structure of a light detection system that detects scattered light and fluorescence are the same as those of the fine particle detector according to the embodiment described first.

The fine particle detector according to the other embodiment uses the cylinder lenses 31 and 32 for which the focusing numerical aperture in the Y-axis direction is reduced relative to the focusing numerical aperture in the X-axis direction to widen a laser spot focused on the sample flow S in the Y-axis direction. The fine particle detector also lets light emitted from the light source 1 pass through the phase difference element 4, provides a phase difference between the wavefronts of light passing through the regions divided in the Y-axis direction, and further widens the laser spot of light focused by the focusing lens 3 in the Y-axis direction.

Figure 5:
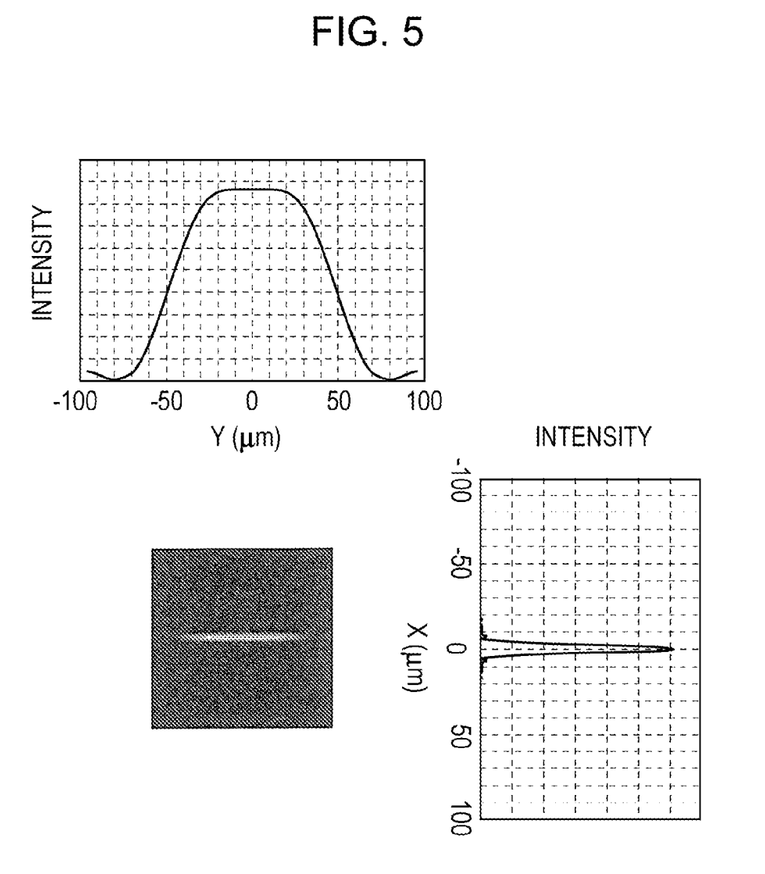
FIG. 5 shows the strength distribution in a laser spot of the fine particle detector according to the other embodiment.

FIG. 5 shows an example of the strength distribution in the laser spot focused on the sample flow S in the fine particle detector according to the other embodiment.

This drawing shows the result of calculation (simulation) for obtaining the strength distribution in the laser spot focused on the sample flow S when the light source 1 of a 638 nm band semiconductor laser has a divergence angle of 8.7 degrees in the X-axis direction and a divergence angle of 23 degrees in the Y-axis direction, the numerical aperture of the collimator lens 2 is 0.25, the numerical aperture of a cylinder lens 31 for focusing in the X-axis direction is 0.67, and the numerical aperture of the cylinder lens 32 for focusing in the Y-axis direction is 0.01. In this calculation, spot diameter d of light passing through the first region 41 is 50% of spot diameter D of light passing through the phase difference element 4.

In this drawing, the laser spot has a Gaussian distribution in the X-axis direction and has a strength distribution that is flat in the middle and uniform over a wide range in the Y-axis direction. In comparison with the simulation result for the fine particle detector according to the embodiment described first in FIG. 3, the width in the X-axis direction is much smaller.

In the fine particle detector according to the other embodiment, spot diameter d of light passing through the first region 41 is preferably 25% to 75% of spot diameter D of light passing through the phase difference element 4. Spot diameter d of light passing through the first region 41 is set to a value in this range, so that light passing through the individual regions can be focused as a laser spot that is flat in the middle and has a consecutively constant strength over a wide range in the Y-axis direction.

As described above, in the fine particle detector according to the other embodiment, a laser can be focused on the sample flow S as a spot that is widened in the Y-axis direction and has a uniform strength distribution over a wide range, and is narrowed in the X-axis direction and has a high optical density. Accordingly, the fine particle detector can make the strength distribution in the laser spot a Gaussian distribution that is widened in the width direction (the Y-axis direction) of the sample flow S, and effectively suppress differences in laser emission strength between fine particles P that are caused by differences in the flow position in the sample flow S. In addition, measurement error caused by differences in the flow positions of fine particles P in the sample flow S can be eliminated. High density light can be emitted to fine particles P to obtain large signal strength. This enables high-precision and high-speed measurement, thereby achieving high detection sensitivity.

As in the fine particle detector according to the embodiment described first, phase differences between the wavefronts of light passing through the first region 41 and the wavefronts of light passing through the second and third regions 42 and 43 can also be caused by liquid crystal molecules with optical anisotropy. In addition, as in the fine particle detector according to the embodiment described first, the number of regions of the phase difference element 4 may be four or more as long as the effects of the other embodiment are ensured, and phase differences caused between the wavefronts of light passing through the regions can be changed if necessary as long as the effects of the other embodiment are ensured.

It should be understood that various changes and modifications to the presently preferred embodiments described herein will be apparent to those skilled in the art. Such changes and modifications can be made without departing from the spirit and scope and without diminishing its intended advantages. It is therefore intended that such changes and modifications be covered by the appended claims.

The application is claimed as follows:

1. A fine particle detector comprising:
a light emitting system letting light from a light source pass through a phase difference element and focusing the light on a sample flow through which fine particles flow, wherein, when the direction of the sample flow is an X-axis direction, the light is emitted to the sample flow in a Z-direction, and a ZX-plane is orthogonal to a Y-direction, then the phase difference element has a plurality of regions divided in the Y-axis direction and causes a phase difference between wavefronts of the light passing through the plurality of regions.

2. The fine particle detector of claim 1, wherein the phase difference element is divided into three regions in the Y-axis direction and causes a phase difference between a wavefront of light passing through a middle region and each of wavefronts of light passing through regions at both ends.

3. The fine particle detector of claim 2, wherein the phase difference caused between the wavefront of the light passing through the middle region and each of the wavefronts of the light passing through the regions at both ends is $\pi$.

4. The fine particle detector of claim 2, wherein a spot diameter of the light passing through the middle region is 25% to 75% of a spot diameter of light passing through the phase difference element.

5. A light emitting apparatus that lets light from a light source pass through a phase difference element having a plurality of regions divided and causing a phase difference between wavefronts of light passing through the plurality of regions and focuses the light on an object, wherein the plurality of regions include a region having a step raised from adjacent regions toward light from the light source and at a height causing the phase difference between the wavefronts of light.

6. The light emitting apparatus of claim 5, wherein the height of the step satisfies:

$$h \times (r-1) = \pi$$

wherein h is the height and r is the refractive index of a material included in the region.

* * * * *